United States Patent [19]

Benjamin

[11] 4,359,053

[45] Nov. 16, 1982

[54] MEANS OF FASTENING SILICONE TUBING TO A RIGID SURGICAL NEEDLE

[75] Inventor: Thomas A. Benjamin, Newcomerstown, Ohio

[73] Assignee: Snyder Laboratories, Inc., New Philadelphia, Ohio

[21] Appl. No.: 156,837

[22] Filed: Jun. 5, 1980

[51] Int. Cl.$^3$ .............................................. A61B 17/06
[52] U.S. Cl. ............................ 128/339; 128/DIG. 21
[58] Field of Search ....... 128/350, 214, 339, DIG. 21; 223/102–104; 285/DIG. 22, 382, 312.4, 345, 305, 239

[56] References Cited

U.S. PATENT DOCUMENTS

| 2,802,468 | 8/1957 | Everett | 128/339 |
| 3,462,361 | 8/1969 | Greenwalt | 128/214 R |
| 4,140,125 | 2/1979 | Smith | 128/339 X |

Primary Examiner—Stephen C. Pellegrino
Attorney, Agent, or Firm—Margaret L. Geringer; Richard H. Brink

[57] ABSTRACT

The invention disclosed is a means of fastening flexible elastic tubing, such as silicone rubber, to a rigid connector. The invention allows for a liquid and gas tight, secure connection without the use of any bonding materials between the tube and the connector and without any external ribbing, threading, texturing, barbing, etc. of any kind on the connector and without any external clamping mechanism used to keep the tubing firmly attached to the rigid connector.

The invention allows for the rigid connector portion of a component, such as a wound drainage surgical needle, to have a very smooth cylindrical surface. The use of a smooth surface with no other adhering mechanism to assist in making a secure connection that will not easily pull off is contrary to what is taught in the art.

5 Claims, 9 Drawing Figures

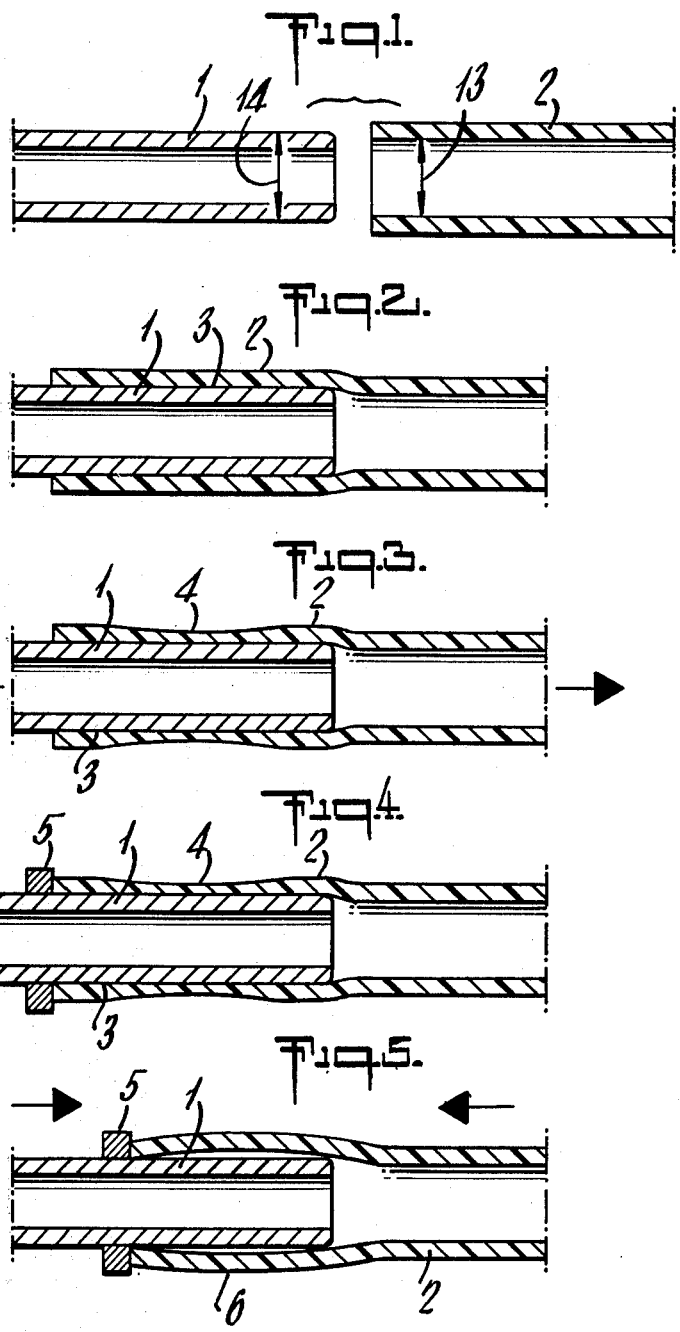

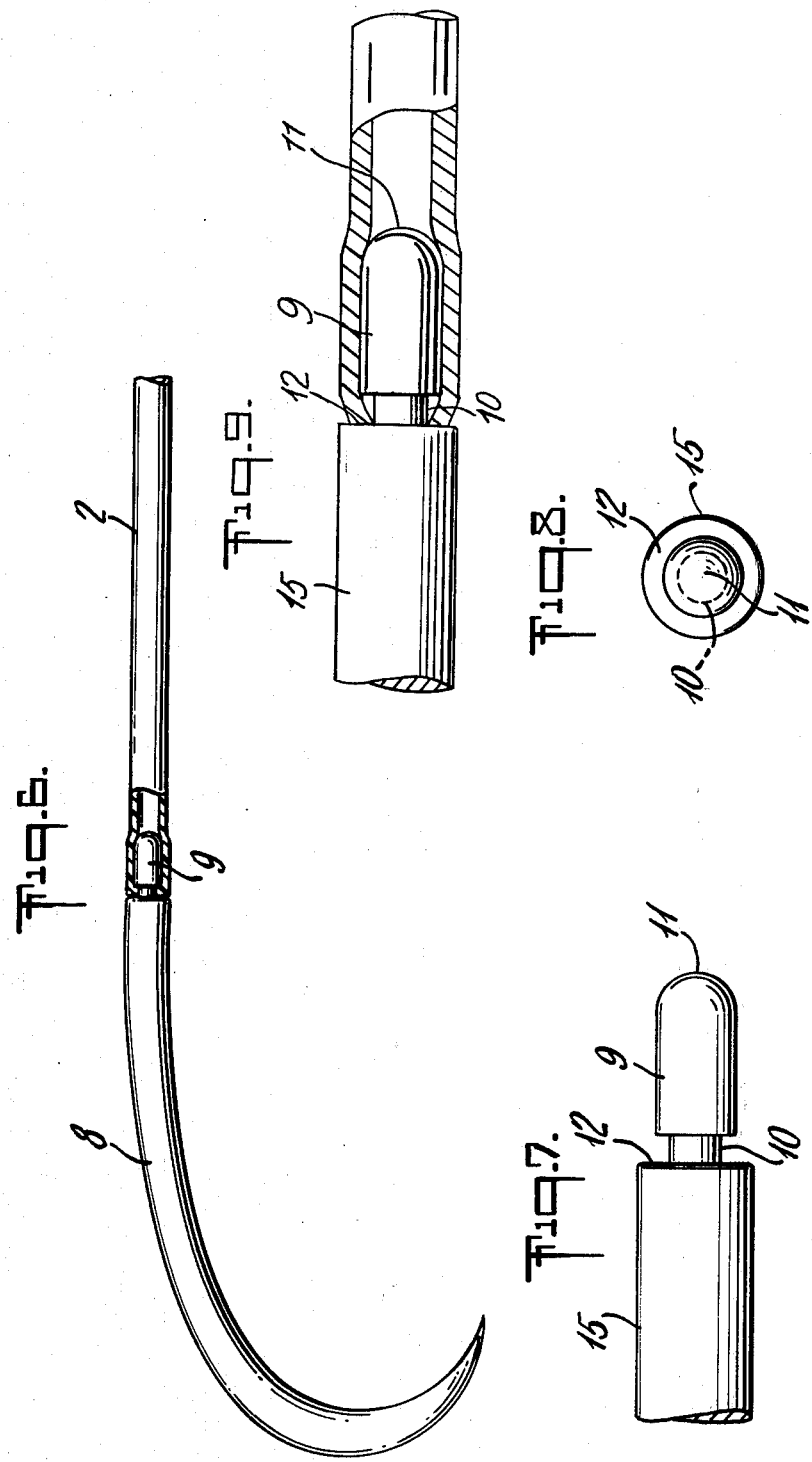

MEANS OF FASTENING SILICONE TUBING TO A RIGID SURGICAL NEEDLE

BACKGROUND OF THE INVENTION

Throughout industry, it is found necessary to connect or otherwise fasten flexible tubing to rigid components to make hook-ups for the transfer of liquids and gases or to complete an assembly with a termination or plug. This has been accomplished by utilizing various configurations, depending upon the permanence and security of the connection desired.

Temporary connections usually can be made by sliding the flexible tubing over a smooth walled rigid component or tube with the component outside diameter slightly larger than the tube inside diameter, relying upon the dimensional interference of the two mating parts to stretch the flexible tube radially. The resilience of the tube then provides a gas or liquid tight seal while still providing the ability to separate and reconnect the parts with relative ease. Typically, this type of connection will disconnect with a minimal longitudinal pulling force on the tubing.

Consequently, in order to provide for more secure connections or permanent connections various additional design features were developed to enhance the security of the connection. Often, the rigid component will utilize a barbed, threaded, ribbed, textured, etc., configuration for a mechanical interference or "bite" between the inner wall of the flexible tube and the outer surface of the rigid part. Such a connection makes separation of the two parts much more difficult, and for total security the tubing can be clamped or bonded to the rigid component.

These methods of making tubing connections to rigid connectors are common in the medical industry, utilizing flexible tubing fabricated of polyethylene, vinyl, polyurethane or latex.

However, with the rapidly increasing usage of flexible silicone rubber tubing, particularly unique problems occur when making a connection between the silicone tubing and a rigid connector. Because of the extremely elastic nature of the material combined with the lubricity of the surface of the material, it has been found that connections made with barbed connectors, threaded connectors, etc., are not secure and are apt to separate when subjected to relatively small tensile stresses. In order to provide secure connections between silicone tubing and other rigid components, these connections are normally bonded with additional silicone adhesive, resulting in a permenent connection, which is expensive, labor consuming and unsightly. Additionally, the only method of separating the silicone tube from such a bonded joint is by cutting the tube from the connector, making the rigid connector unsuitable for reconnection because of the portion of tubing and adhesive remaining on the connector.

OBJECTS AND SUMMARY OF THE INVENTION

It is therefore, a principal object of the invention to provide a means of securely connecting silicone rubber tubing to a rigid connector without the use of silicone adhesive.

It is a further object of the invention to provide a means of securely connecting silicone rubber tubing to a rigid connector without the use of other mechanical locking means such as external texturing on the connector and without the use of any external clamping device over the tube and connector.

It is a still further object of the invention to provide a means of easily separating the silicone tubing from the connector without damage so the parts, both tubing and connector, can be reconnected or connected to other components for additional use.

The present invention accomplishes all of the above objects of invention. Because of the extreme elasticity of silicone rubber, it has been found that subjecting the material to a tensile stress causes a considerable reduction in the cross-sectional dimensions of the material as it elongates. Additionally, when stretched, the surface of the tubing looses some of its lubricity. Utilizing these characteristics, it has been found that a very secure connection can be formed by putting the silicone tubing over a very smooth shank or tube or connector, which is contrary to normal practice. The smoothness of the surface is critical to the security of the connection, such that a highly polished surface will provide a much more secure connection than a rough surface.

DESCRIPTION OF THE DRAWINGS

FIG. 1 is a cross-sectional side elevational view of a portion of a rigid connector and the silicone tubing prior to assembly.

FIG. 2 is a cross-sectional side elevational view of a portion of the rigid connector and the silicone tubing after assembly and before subjecting the joint to a tensile force.

FIG. 3 is a cross-sectional side elevational view of the joint after subjecting the joint to a tensile force.

FIG. 4 is a cross-sectional side elevational view illustrating a rigid flange at the end of the silicone tube.

FIG. 5 is a cross-sectional side elevational view illustrating the expansion of the tubing by applying a compressive force.

FIG. 6 is a side elevational view of a surgical needle having a certain connector embodiment attached to silicone tubing.

FIG. 7 is an enlarged fragmentary side elevational view of the connector embodiment of FIG. 6.

FIG. 8 is an end view of the connector embodiment of FIG. 7.

FIG. 9 is an enlarged view of the connector portion of FIG. 6.

DETAILED DESCRIPTION OF THE INVENTION

FIG. 1 illustrates a rigid component 1 and a piece of silicone tubing 2 prior to assembly. The surface of the component 1 is a very smooth polished surface. The component 1 is preferably made of a metal material. It is necessary that the outside diameter 14 of the rigid component 1 be only slightly larger than the inside diameter 13 of the silicone tubing 2. The elasticity of the silicone tubing 2 allows the tubing 2 to slide onto the connecting end of the component 1 as shown in FIG. 2. The dimensional interference between the two parts causes a seal 3 to form.

FIG. 3 illustrates a longitudinal tensile force being applied to the rubber tubing. The force is illustrated by the arrows in FIG. 3. Any tension applied to the silicone tubing 2 when located on slightly larger component 1 results in an elongation of the silicone tubing 2, causing a tightening of the silicone tubing 2 onto the smooth connecting surface of the component 1, where it grips even more securely because of the surface change of the silicone tubing 2. The elongation of the tubing 2 results in a decreased diameter 4 of the silicone tubing 2, increasing the security of the seal 3. Additionally, it has been found that this elastic deformation of the silicone tubing 2 will be localized at the portion of the tubing over the rigid component 1 and it will remain in a locally deformed state after the tensile force is removed from the remainder of the tube. Therefore, the tubing 2 can be stretched and pulled after assembly to the rigid component 1, resulting in a more secure grip even after releasing the tensile stress. With appropriate relative sizing of the silicone tubing 2 and the rigid connector 1, the two parts can be joined, in such a manner, so securely they cannot be separated by manually pulling. Additional tensile force makes the joint more secure.

This secure joint is formed using a connector component 1 with a perfectly smooth surface, and utilizes no additional mechanical locking or bonding means. The use of a plain smooth surface is contrary to normal practice for forming a tight, secure connection.

In order to detach the silicone tubing 2 from the component 1, a longitudinally compressive force is applied to the tubing 2. The force is illustrated by the arrows in FIG. 5. This force should be applied against a stop means, to prevent the tubing 2 from sliding farther onto the component 1. The longitudinally compressive force causes tubing 1 to de-elongate and hence returns the tubing diameter back to its original diameter prior to the elongation. The tubing also regains its surface lubricity which it lost upon elongation of the tubing 2.

Ones fingers can easily be used as a stop means by placing your fingers at the end of the tubing 2 and then applying the compressive force. Alternatively, a rigid flange 5, can be used as stop means as shown in FIGS. 4 and 5.

The joint can then be easily separated by applying a compressive force inwardly toward the axis of the rigid component 1 on the portion of the tube 2 covering the rigid component 1. This can be easily accomplished with one's fingers. Simultaneously with the inward compressive force in the area stated, an additional longitudinally directed force is also applied to the portion of the tube 2 covering the rigid component 1 to effect removal of the tubing from the connector component 1.

FIGS. 6, 7 and 8 illustrate a particular embodiment of a cylindrical surgical needle 8. The connector portion 9 of the needle 8 has a semi-spherical contour 11 on one end which allows for easier engagement of the tubing 2 to the connector 9. The needle 8 includes a neck 10 which protrudes from the opposite end of the connector 9. The neck 10 has a smaller diameter than the connector 9. The neck 10 attaches the connector 9 to the body 15 of the needle 8. The necked in portion 10 is a means of providing a relieved area permitting the silicone tubing to relax to its original diameter. The body 15 has a larger diameter than either the connector 9 or neck 10. This allows the outer diameter of the relaxed portion of the tubing 2 to be flush with the cylindrical body 15 of the needle. Therefore, the end of the tubing does not protrude above the body portion. The end surface 12 of the body 15 of the needle 8 acts as a flange for the tubing 2 to mate against. Therefore, when removing the tubing 2, the longitudinally compressive force can be applied against this flat end surface 12 to act as a stop means.

The invention described allows for a secure seal between silicone tubing and a rigid component, such as a metal surgical needle, without the using of a silicone adhesive or any other mechanical locking means. The invention also allows both the tubing and connecting component to be reused. While this invention has been described and exemplified in terms of its preferred embodiment, those skilled in the art can appreciate that modifications can be made without departing from the spirit and scope of this invention.

I claim:

1. A cylindrical metal surgical needle for secure attachment to flexible silicone tubing without the use of any bonding materials, said needle comprising at one end a rigid, smooth cylindrical connector portion having no external surface texturing and no additional mechanical locking features, said connector portion having a diameter greater than the inner diameter of the tubing to be attached to said connector and wherein said connector has a semi-spherical contour on one end which allows for easier engagement of the tubing to the connector and a neck portion of smaller diameter and length protruding from the opposite end of the connector and wherein said neck attached the connector to a cylindrical body portion of the needle and wherein said neck portion is a means of providing a relieved area permitting the silicone tubing to relax to its original diameter, and wherein the body portion has a diameter larger than the connector to allow the outer diameter of the tubing to be substantially flush with the cylindrical surface of the body of the needle and also to act as a rigid stop means for the tubing to mate against.

2. A method of connecting silicone rubber tubing to a cylindrical metal surgical needle without the use of any bonding materials, said needle having at one end a rigid, smooth cylindrical connector portion having no external surface texturing and no additional mechanical locking features, said connector portion having a diameter greater than the inner diameter of the tubing to be attached to said connector and wherein said connector has a semi-spherical contour on one end which allows for easier engagement of the tubing to the connector and a neck portion of smaller diameter and length protruding from the opposite end of the connector and wherein said neck attaches the connector to a cylindrical body portion of the needle and wherein said neck portion is a means of providing a relieved area permitting the silicone tubing to relax to its original diameter, and wherein the body portion has a diameter larger than the connector to allow the outer diameter of the tubing to be substantially flush with the cylindrical surface of the body of the needle and also to act as a rigid stop means for the tubing to mate against, and comprising the steps of:

(a) Sliding the silicone tubing onto the smooth, cylindrical connector to mate against the rigid stop means; and (b) Applying a longitudinal tensile force to the silicone rubber tubing to cause elongation of the tube and reduce the diameter of a portion of the tube, and thereby creating a firm no-slip adherence of the silicone rubber tubing to the connector.

3. A method of firmly attaching and subsequently detaching silicone rubber tubing to a cylindrical metal surgical needle without the use of any bonding materials, said needle having at one end a rigid, smooth cylindrical connector portion having no external surface texturing and no additional mechanical locking features, said connector portion having a diameter greater than the inner diameter of the tubing to be attached to said connector and wherein said connector has a semispherical contour on one end which allows for easier engagement of the tubing to the connector and a neck portion of smaller diameter and length protruding from the opposite end of the connector and wherein said neck attaches the connector to a cylindrical body portion of the needle and wherein said neck portion is a means of providing a relieved area permitting the silicone tubing to relax to its original diameter, and wherein the body portion has a diameter larger than the connector to allow the outer diameter of the tubing to be substantially flush with the cylindrical surface of the body of the needle and also act as a rigid stop means for the tubing to mate against, and comprising the steps of:
  (a) Sliding the silicone tubing onto the smooth, cylindrical connector to mate against the rigid stop means;
  (b) Applying a longitudinal tensile force to the silicone rubber tubing to cause elongation of the tube and reduce the diameter of a portion of the tube, and thereby creating a firm no-slip adherence of the silicone tubing to the connector; and when ready for detaching;
  (c) Applying a longitudinal compressive force to the tubing against said stop means to de-elongate the tubing and return the diameter back to its original diameter; and
  (d) Applying compressive pressure inwardly toward the rigid connector on the portion of the tube covering the rigid connector on the portion of the tube covering the rigid connector and simultaneously applying force directed longitudinally to remove the tubing from the connector.

4. A method of connecting silicone rubber tubing to a cylindrical metal surgical needle without the use of any bonding materials said needle having at one end a rigid, smooth cylindrical connector portion having no external surface texturing and no additional mechanical locking features, said connector portion having a diameter greater than the inner diameter of the tubing to be attached to said connector wherein said method comprises the steps of:
  (a) Sliding the silicone tubing onto the smooth, cylindrical connector portion; and
  (b) Applying a longitudinal tensile force to the silicone rubber tubing to cause elongation of the tube and reduce the diameter of a portion of the tube, and thereby creating a firm no-slip adherence of the silicone rubber tubing to the connector.

5. A method of firmly attaching and subsequently detaching silicone rubber tubing to a cylindrical metal surgical needle without the use of any bonding materials said needle having at one end a rigid, smooth cylindrical connector portion having a diameter greater than the inner diameter of the tubing to be attached to said connector wherein said method comprises the steps of:
  (a) Sliding the silicone tubing onto the smooth, cylindrical connector portion; and
  (b) Applying a longitudinal tensile force to the silicone rubber tubing to cause elongation of the tube and reduce the diameter of a portion of the tube, and thereby creating a firm no-slip adherence of the silicone tubing to the connector; and when ready for detaching;
  (c) Applying a longitudinal compressive force to the tubing against a stop means to de-elongate the tubing and return the diameter back to its original diameter; and
  (d) Applying compressive pressure inwardly toward the rigid connector on the portion of the tube covering the rigid connector and simultaneously applying force directed longitudinally to remove the tubing from the connector.

* * * * *